US010329254B2

(12) United States Patent
Diodato et al.

(10) Patent No.: US 10,329,254 B2
(45) Date of Patent: Jun. 25, 2019

(54) PROCESS FOR THE PREPARATION OF 6-CHLORO-2,3,4,9-TETRAHYDRO-1H-CARBAZOLE-1-CARBOXAMIDE AND INTERMEDIATES THEREOF

(71) Applicant: AOP ORPHAN PHARMACEUTICALS AG, Vienna (AT)

(72) Inventors: Enrica Diodato, Siena (IT); Katia Marcucci, Siena (IT); Russell Thomas, Siena (IT); Paul Wiedenau, Siena (IT); Martin Rettig, Schwanau-nonnenweier (DE); Huw Roberts, Flint Wales (GB)

(73) Assignee: AOP ORPHAN PHARMACEUTICALS AG, Vienna (AT)

( * ) Notice: Subject to any disclaimer, the term of this patent is extended or adjusted under 35 U.S.C. 154(b) by 0 days.

(21) Appl. No.: 15/134,028

(22) Filed: Apr. 20, 2016

(65) Prior Publication Data
US 2016/0304455 A1    Oct. 20, 2016

Related U.S. Application Data

(63) Continuation of application No. 14/352,623, filed as application No. PCT/EP2012/070769 on Oct. 19, 2012, now abandoned.

(30) Foreign Application Priority Data

Oct. 20, 2011   (EP) .................................. 11185959

(51) Int. Cl.
    *C07D 209/88*        (2006.01)
(52) U.S. Cl.
    CPC ................... *C07D 209/88* (2013.01)
(58) Field of Classification Search
    USPC ........................................................ 548/448
    See application file for complete search history.

(56) References Cited

U.S. PATENT DOCUMENTS

| 3,769,298 A | 10/1973 | McManus et al. |
| 3,956,295 A | 5/1976 | Biere |
| 4,057,640 A | 11/1977 | Biere |
| 8,084,640 B2 | 12/2011 | Broell |
| 8,486,990 B2 | 7/2013 | Napper et al. |

| 2005/0163820 A1 | 7/2005 | Fischer |
| 2008/0081910 A1 | 4/2008 | Sabb |
| 2009/0306168 A1 | 12/2009 | Napper et al. |
| 2010/0081696 A1 | 4/2010 | Berthelette |

FOREIGN PATENT DOCUMENTS

| CA | 1053682 A | 5/1979 |
| CA | 1057753 A | 7/1979 |
| DE | 2431292 A1 | 1/1976 |
| JP | S43-24914 | 10/1968 |
| JP | S50-069072 A | 6/1975 |
| JP | S51-12538 A | 11/1976 |
| JP | S51-125072 A | 11/1976 |
| JP | 2000-026416 A | 1/2000 |
| JP | 2002-512225 A | 4/2002 |
| JP | 2006-516254 A | 6/2006 |
| JP | 2006-520301 A | 9/2006 |
| JP | 2007-519473 A | 7/2007 |
| JP | 2007-531015 A | 11/2007 |
| JP | 2008-504823 A | 2/2008 |
| WO | WO 99/54300 A1 | 10/1999 |
| WO | WO 2004/063155 A1 | 7/2004 |
| WO | WO 2005/026112 A2 | 3/2005 |
| WO | WO 2005/072408 A2 | 8/2005 |
| WO | WO 2006/065480 A2 | 6/2006 |
| WO | WO 2006/099245 A1 | 9/2006 |
| WO | WO 2007/047604 A2 | 4/2007 |
| WO | WO 2008/019825 A1 | 2/2008 |

OTHER PUBLICATIONS

Gassman et al., "A General Mehtod for the Synthesis of Indoles," Journal of the American Chemical Society, Aug. 21, 1974, pp. 5495-5508, 96:17.
Hansch et al., "Catalytic Synthesis of Heterocycles, VIII, Dehydrocyclization of Anils to Acridine and Carbazole," Journal of the American Chemical Society, Mar. 22, 1952, pp. 4554-4555, 74.
International Search Report issued in European Patent Application No. PCT/EP2012/070769 dated Dec. 20, 2012.
Napper, et al., "Discovery of Indoles as Potent and Selective Inhibitors of the Deacetylase SIRT1," Journal of Medicinal Chemistry, XP-002414402, 2005, pp. 8045-8054, vol. 48, No. 25.
Sheehan et al., "The O-Alkylation of 2-Carbethoxycyclohexanone," J. Am. Chem. Soc., May 1950, pp. 2127-2129, vol. 72, No. 5.

*Primary Examiner* — Nyeemah A Grazier
(74) *Attorney, Agent, or Firm* — Arent Fox LLP

(57) ABSTRACT

The invention relates to a novel process for the preparation of rac-6-Chloro-2,3,4,9-tetrahydro-1H-carbazole-1-carboxamide (I) in pharmaceutically acceptable polymorphic form, through the conversion of a 3-bromo-2-oxo-cyclohexanecarboxylic acid alkyl ester into 6-chloro-2,3,4,9-tetrahydro-1H-carbazole-1-carboxylic acid alkyl ester, which in turn is processed to yield the final product.

18 Claims, 11 Drawing Sheets

PROCESS FOR THE PREPARATION OF 6-CHLORO-2,3,4,9-TETRAHYDRO-1H-CARBAZOLE-1-CARBOXAMIDE AND INTERMEDIATES THEREOF

CROSS-REFERENCE TO RELATED APPLICATIONS

This application is a Continuation of U.S. patent application Ser. No. 14/352,623, filed Apr. 17, 2014, which is a National Stage entry of International Application No. PCT/EP2012/070769, filed Oct. 19, 2012, which claims priority to European Patent Application No. 111859591, filed Oct. 20, 2011. The disclosures of the prior applications are hereby incorporated in their entirety by reference.

The present invention relates to a novel process for the preparation of rac-6-Chloro-2,3,4,9-tetrahydro-1H-carbazole-1-carboxamide (I) in pharmaceutically acceptable polymorphic form and to intermediates thereof.

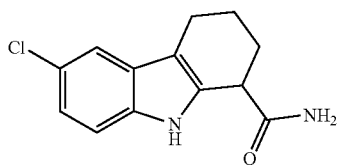

I

BACKGROUND TO THE INVENTION

The compound 6-Chloro-2,3,4,9-tetrahydro-1H-carbazole-1-carboxamide (I) is known from WO2005026112 to possess anti Sirt1 activity, and as such useful in the preparation of medicaments for any condition which may benefit from the inhibition of Sirt1. These not limitedly include cancer, metabolic diseases such as metabolic syndrome, type I diabetes or type II diabetes, obesity, dislipidemia, hyperlipidemia, Alzheimer's disease, Parkinson's disease, amyotrophic lateral sclerosis, neurodegenerative conditions that are caused at least in part by polyglutamine aggregation, such as Huntington's disease, spinalbulbar muscular atrophy (SBMA or Kennedy's disease) dentatorubro-pallidoluysian atrophy (DRPLA), spinocerebellar ataxia 1 (SCA1), spinocerebellar ataxia 2 (SCA2), Machado-Joseph disease (MJD; SCA3), spinocerebellar ataxia 6 (SCA6), spinocerebellar ataxia 7 (SCAT), and spinocerebellar ataxia 12 (SCA12).

Compound (I) can be isolated, depending on the method of preparation, in crystalline form A or B or in amorphous form.

Form A is a solvent-free (FIG. 1), non hygroscopic (FIG. 2) form that can be obtained by crystallisation from isopropanol or by concentration at room temperature from various polar protic solvents such as methanol, ethanol, isopropanol or water, as well as from ethyl acetate. Form A is characterised by an X ray diffraction pattern shown in FIG. 3 having prominent peaks as set out in table 1 below:

TABLE 1

| °2θ | d space (Å) | Intensity (%) |
| --- | --- | --- |
| 11.37 ± 0.20 | 7.783 ± 0.139 | 69 |
| 13.26 ± 0.20 | 6.677 ± 0.102 | 31 |
| 16.50 ± 0.20 | 5.373 ± 0.065 | 27 |
| 17.76 ± 0.20 | 4.994 ± 0.056 | 19 |

TABLE 1-continued

| °2θ | d space (Å) | Intensity (%) |
| --- | --- | --- |
| 22.02 ± 0.20 | 4.037 ± 0.037 | 29 |
| 22.77 ± 0.20 | 3.905 ± 0.034 | 100 |
| 24.18 ± 0.20 | 3.681 ± 0.030 | 29 |
| 24.54 ± 0.20 | 3.628 ± 0.029 | 71 |

An IR absorbtion spectrum shown in FIG. 4 having characteristic peaks expressed in cm$^{-1}$ at approximately 3448, 3307, 3277, 1649, 1306 and 772

A Raman spectrum shown in FIG. 5 having characteristic peaks expressed in cm$^{-1}$ at approximately 3450, 3050, 1649, 1616, 1476, 1307, 1194, 901, 831, 323 and 197.

(The term approximately means in this context that the values can vary, e.g. by up to ±4 cm$^{-1}$)

A melting point of about 183° C.

Form B (TGA and DSC curves in FIG. 6) is a non hygroscopic form (FIG. 7) that can be obtained by evaporation at room temperature from acetone or MEK (methyl ethyl ketone), or a mixture of solvents which contain acetone or MEK.

Form B is characterised by:

an X ray diffraction pattern shown in FIG. 8 having prominent peaks as set out in table 2 below

TABLE 2

| °2θ | d space (Å) | Intensity (%) |
| --- | --- | --- |
| 10.86 ± 0.20 | 8.147 ± 0.152 | 90 |
| 14.73 ± 0.20 | 6.014 ± 0.082 | 18 |
| 15.42 ± 0.20 | 5.746 ± 0.075 | 35 |
| 17.19 ± 0.20 | 5.159 ± 0.060 | 67 |
| 17.91 ± 0.20 | 4.953 ± 0.055 | 51 |
| 21.27 ± 0.20 | 4.177 ± 0.039 | 28 |
| 21.69 ± 0.20 | 4.097 ± 0.038 | 25 |
| 22.50 ± 0.20 | 3.952 ± 0.035 | 18 |
| 24.18 ± 0.20 | 3.681 ± 0.030 | 15 |
| 25.50 ± 0.20 | 3.493 ± 0.027 | 100 |

An IR absorbtion spectrum shown in FIG. 9 having characteristic peaks expressed in cm$^{-1}$ at approximately 3389, 1683, 1405 and 1313

A Raman spectrum shown in FIG. 10 having characteristic peaks expressed in cm$^{-1}$ at approximately 1712, 1623, 1485, 1313, 1163, 843, 339 and 212.

(The term approximately means in this context that the values can vary, e.g. by up to +/−4 cm$^{-1}$)

A melting point of about 165° C.

The amorphous form of (I) is characterised by the lack of sharp X-ray diffraction peaks in its XRPD pattern (FIG. 11) and can be obtained by cryogrinding.

The amorphous form can easily be converted into form A or into form B. This can be achieved by slurrying in ethanol or acetone, towards forms A or B, respectively. In turn, form B can be easily converted into form A. This can be achieved by slurrying form B in water at various temperatures.

Form A is non hygroscopic (FIG. 2), stable over time (Tables 3 and 4) and it is suitable for use in pharmaceutical compositions.

Form A can be suitably formulated into various pharmaceutically acceptable preparations, which are preferably for oral administration.

A three-step method for the preparation of (I) is described in Napper et al. ("Discovery of Indoles as Potent and Selective Inhibitors of the Deacetylase SIRT1." Journal of Medicinal Chemistry 48.25 (2005): 8045-054.).

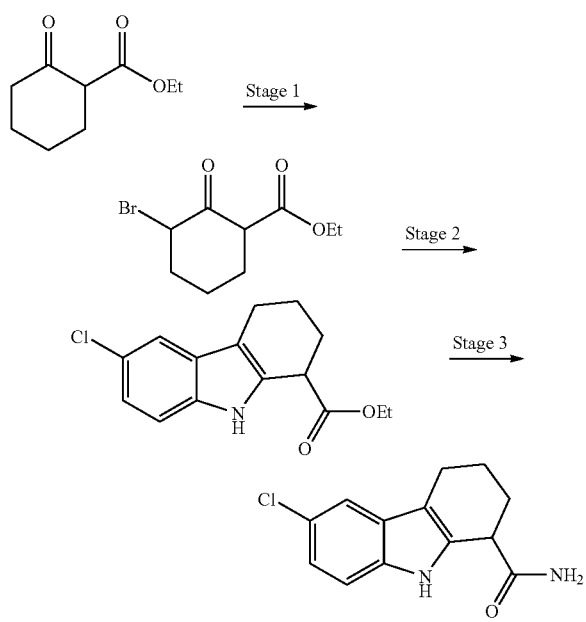

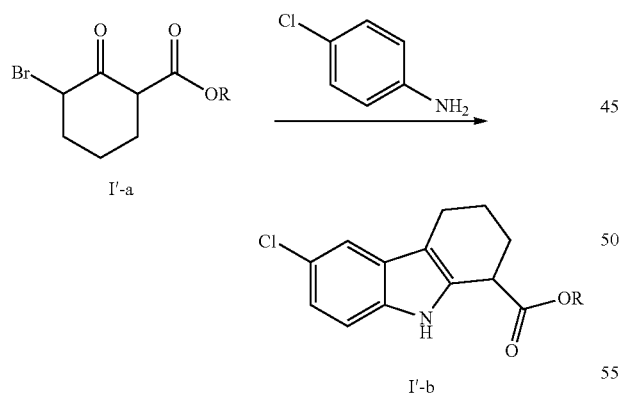

This method is however not amenable to large scale production. One drawback of the known method is the need for chromatographic purification of the intermediates. Another drawback is the use of ethyl ether as a solvent in the first step, which is hazardous on technical scale. Another major limiting factor is the presence of a highly exothermic second step, which is incompatible with the safety requirements of large scale production. Particularly, stage 2 of the process disclosed in Napper et al, wherein a compound of formula I'-a wherein R is ethyl is converted into a compound of formula I-b' using unsolvated reactants, involves an uncontrollable exotherm which makes the process unsafe on a technical scale.

DESCRIPTION OF THE INVENTION

The present invention provides a process for obtaining compound (I) which avoids the drawbacks in the prior art and which is conveniently applicable on a technical scale.

We have surprisingly found that the reaction between compound (I'-a) and 4-chloroaniline can be carried out in far safer conditions under heating using a solvent which forms an azeotropic mixture with water.

Accordingly, in a first embodiment the invention provides a process for the preparation of intermediate (I'-b) according to the following scheme:

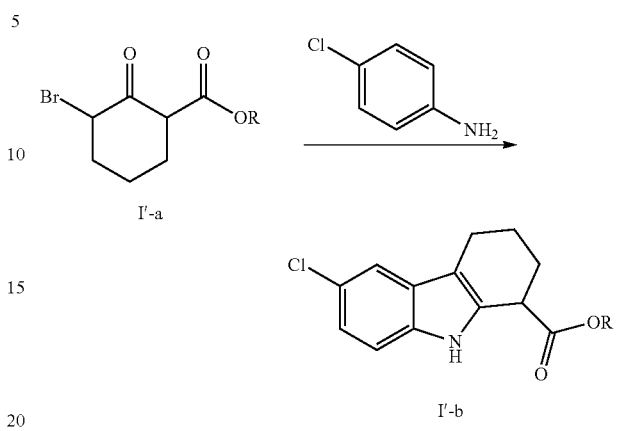

wherein R is $C_1$-$C_6$ linear, branched or cyclic alkyl chain and preferably ethyl, said process being characterised in that the reaction between (I'-a) and 4-chloroaniline is performed under heating in a solvent which forms an azeotropic mixture with water and which is preferably selected from xylenes, chlorobenzene, cyclohexane, ethyl acetate, MTBE, toluene and preferably ethanol.

When the conditions described above are used, the process can be lengthy: we have determined that up to 56 hrs can be necessary for a kg-scale reaction to reach completion. We have found that the elimination of water by azeotropic distillation significantly reduces the reaction time (see examples 3 and 4). Best results can be achieved by performing at least two azeotropic distillations of the reaction mixture.

Accordingly, in a preferred embodiment, the process for the preparation of compound (I'-b) as above defined further comprises removing water from the reaction mixture by azeotropic distillation.

We have also determined that the chromatographic purification of (I'-b) can be avoided if the crude product is crystallised from an apolar solvent such as cyclohexane. Accordingly, in a further preferred embodiment, the crude mixture containing compound (I'-b) obtained by the invention process is crystallized from an apolar solvent, preferably from cyclohexane (see examples 3 and 4).

In a further embodiment of the invention, the intermediate (I'-b) is converted into compound (I):

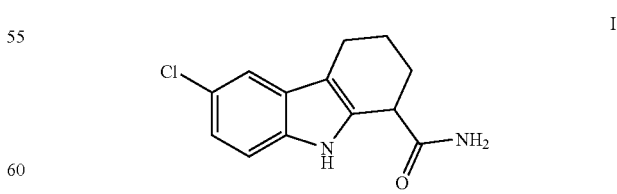

by reaction with ammonia in a suitable solvent. The skilled chemist may easily replace this step by a two-step procedure involving the reaction between (I'-b) and suitably protected amine derivative followed by deprotection of this amine in order to obtain (I).

The choice of the solvent in which to perform conversion step (I'-b)→(I) influences the reaction yield. We have determined that this step should not be performed using water as solvent because part of the ester (I'-b) converts to its free acid equivalent. Particularly suitable solvents in which to perform the reaction are ethanol and methanol, the latter being preferred in that, the reaction reaches completion in shorter times. When using methanol, ammonia may be added either pure or as a methanolic solution, the former being preferred (examples 5 and 6).

Compound (I) may be further processed by:
a) removing any unreacted ammonia from the reaction mixture
b) precipitating the compound from the reaction mixture
c) recrystallising the precipitate from a suitable solvent so as to obtain the compound of formula (I) in the crystalline form A.

Step a) may be performed by evaporation under reduced pressure and/or heating and/or sparging the reaction mixture with an inert gas.

Step b) may be performed by addition of water to the reaction mixture. Exemplary suitable solvents in step c) are ethyl acetate, water, methanol, ethanol and isopropanol, with isopropanol being preferred.

Should one wish to obtain GMP-grade form A, it may be preferable to perform two or more subsequent crystallizations. We have determined that GMP-grade material can be obtained after only two re-crystallisations if the crude precipitate ensuing from step b) is crystallised from MEK/cyclohexane before performing step c) (example 7).

Thus, the process of the invention does not require chromatographic purification of the final product and allows to obtain (I) in crystalline form A.

The starting compound (I'-a) can be obtained by reacting equimolar amounts of bromine and a compound of formula I'-c, at 0-5° C. in DCM:

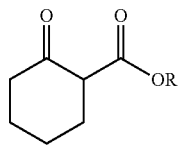

I'-c

Alternatively, the compound (I-a') is obtained by slow addition, under stirring, of gaseous bromine to a solvent-free equimolar amount of compound (I'-c), at 0-10° C.

In either way, the use of the solvent ethyl ether, which is hazardous on a technical scale, is avoided, and the impact on the environment is reduced by eliminating the amount of chlorinated solvent waste.

The invention will be further illustrated by the following examples and attached figures.

EXAMPLES

Figure 1:
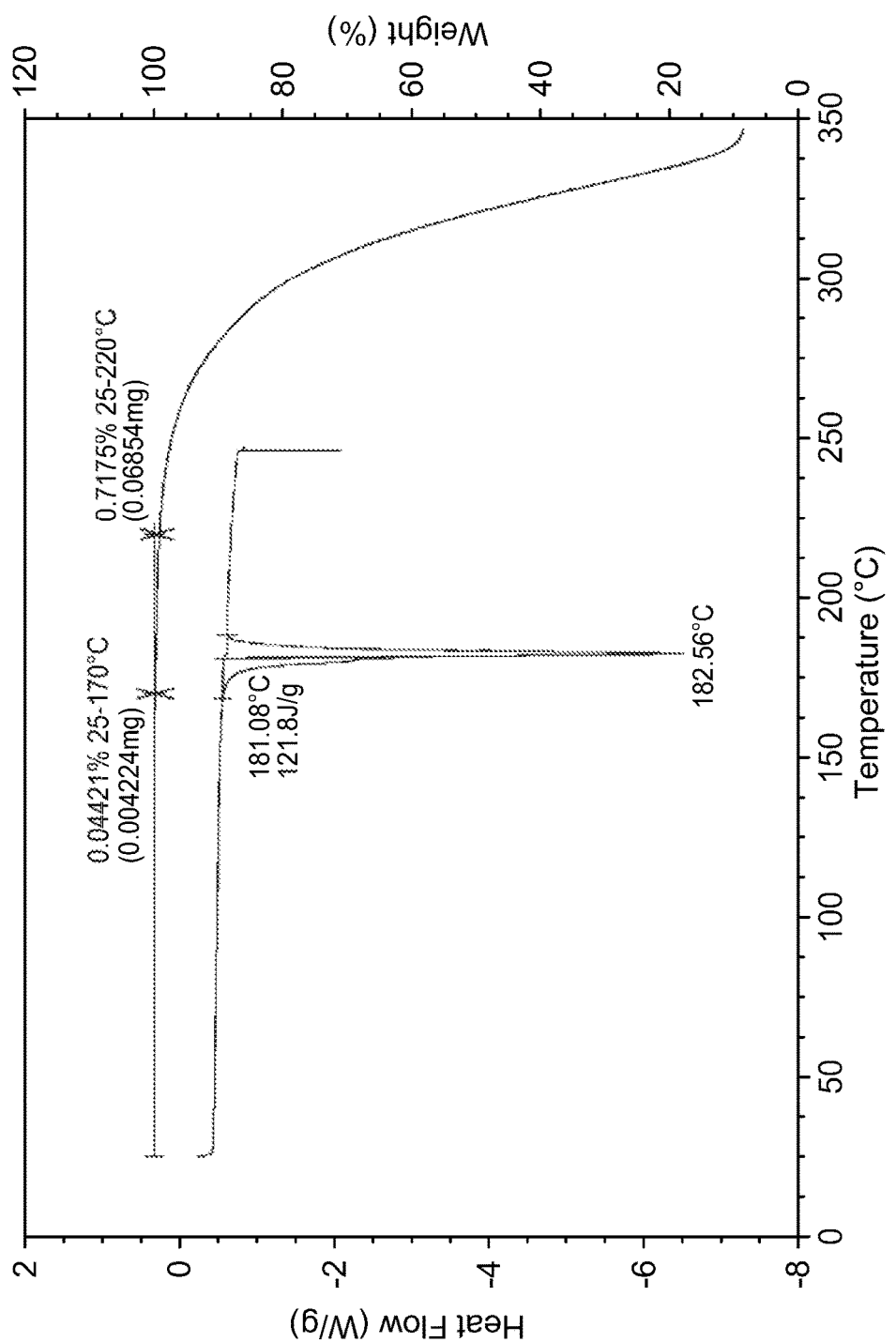
FIG. 1: DSC (upper) and TGA (lower) curves of form A
Figure 2:
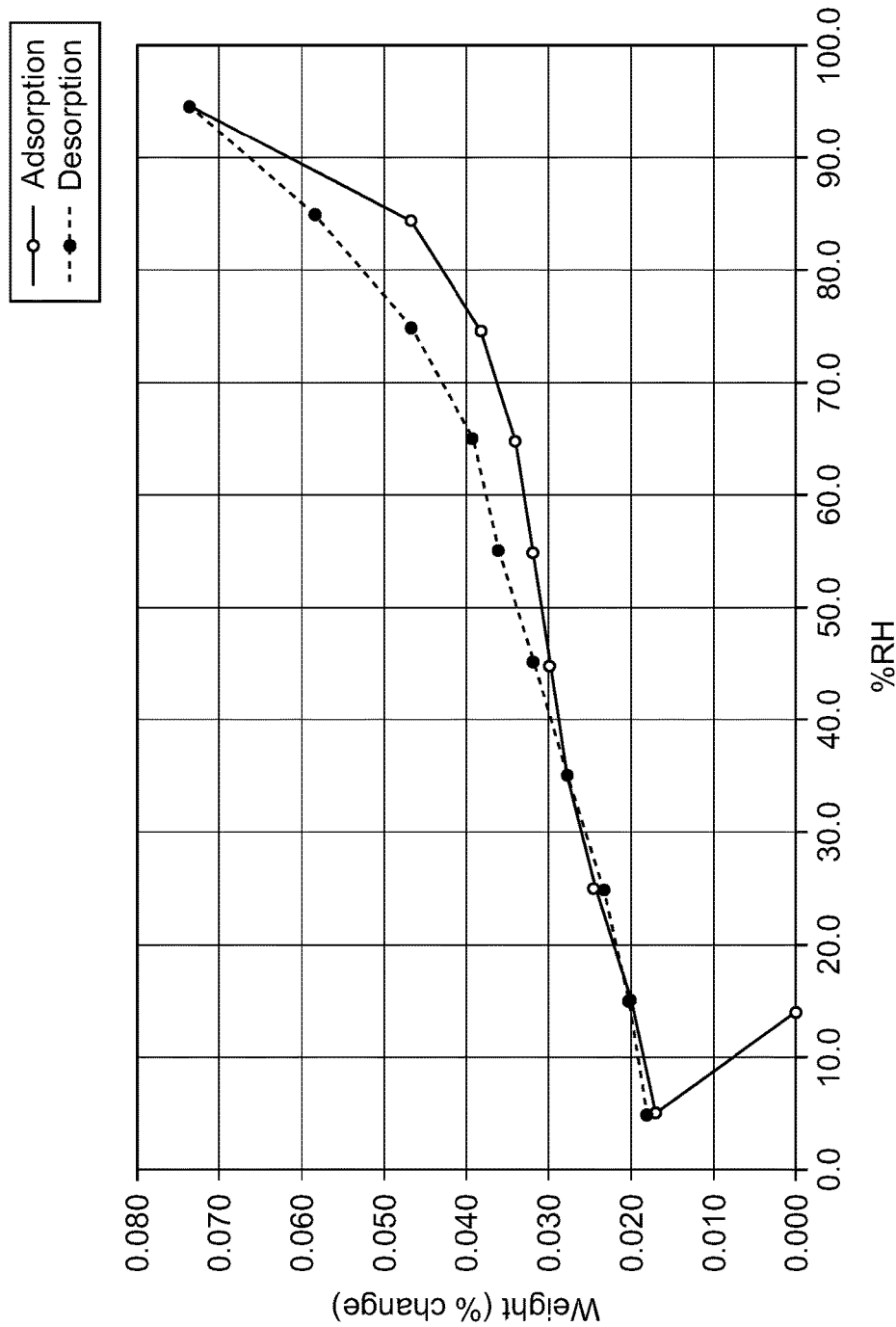
FIG. 2: Absorption-Desorption spectrum of form A
Figure 3:
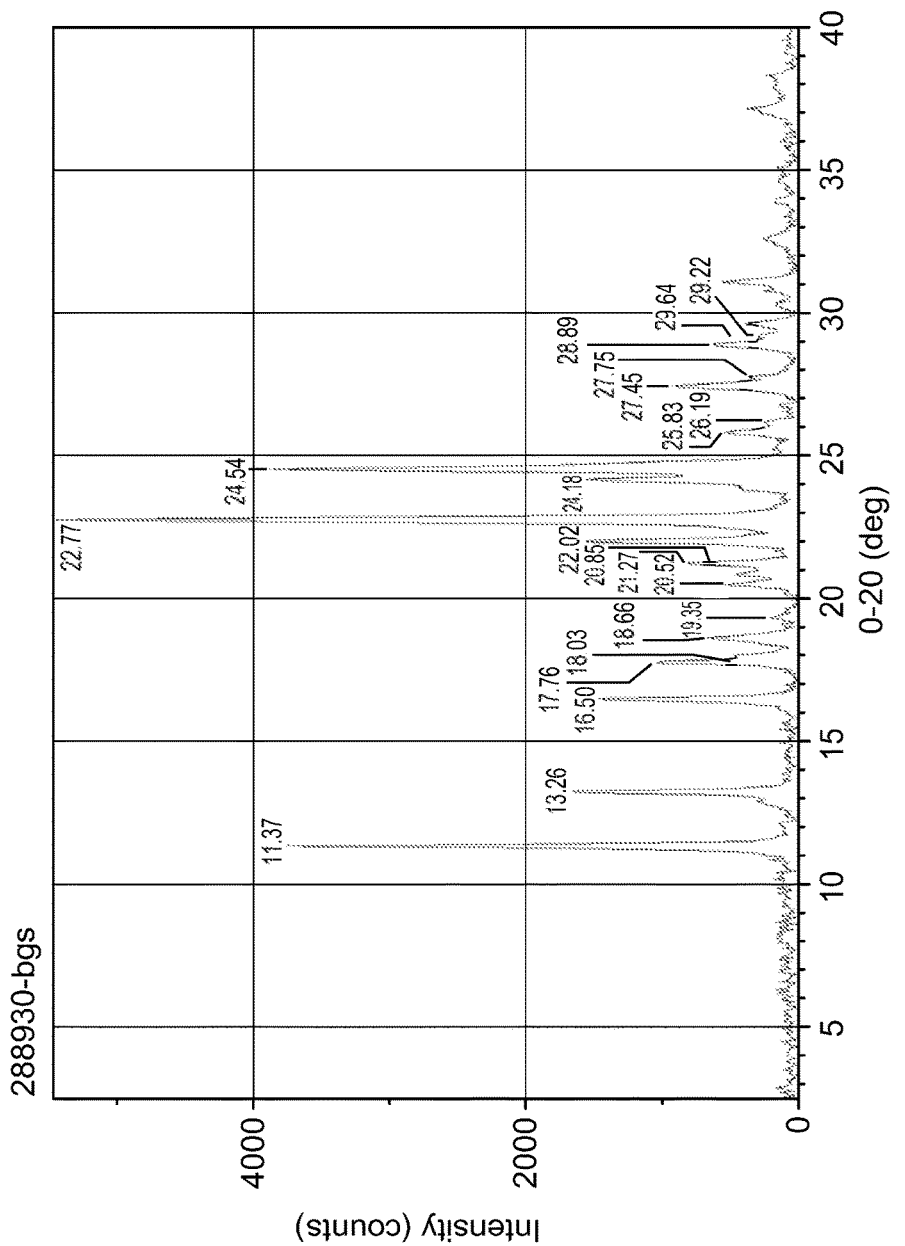
FIG. 3: XPRD spectrum of form A. The peak assignments in this figure were picked automatically and no attempt was made to determine "representative" peaks.
Figure 4:
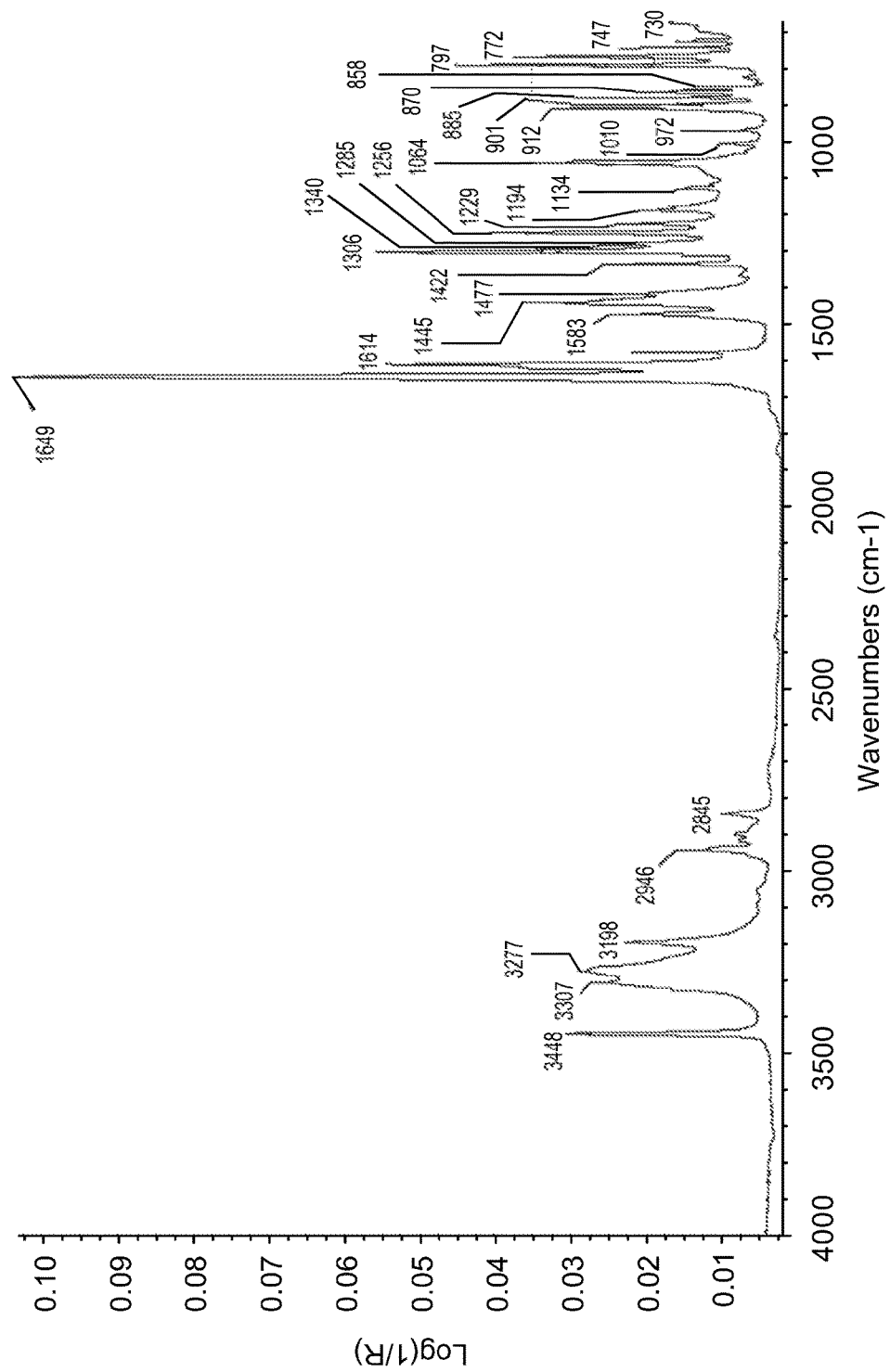
FIG. 4: IR spectrum of form A
Figure 5:
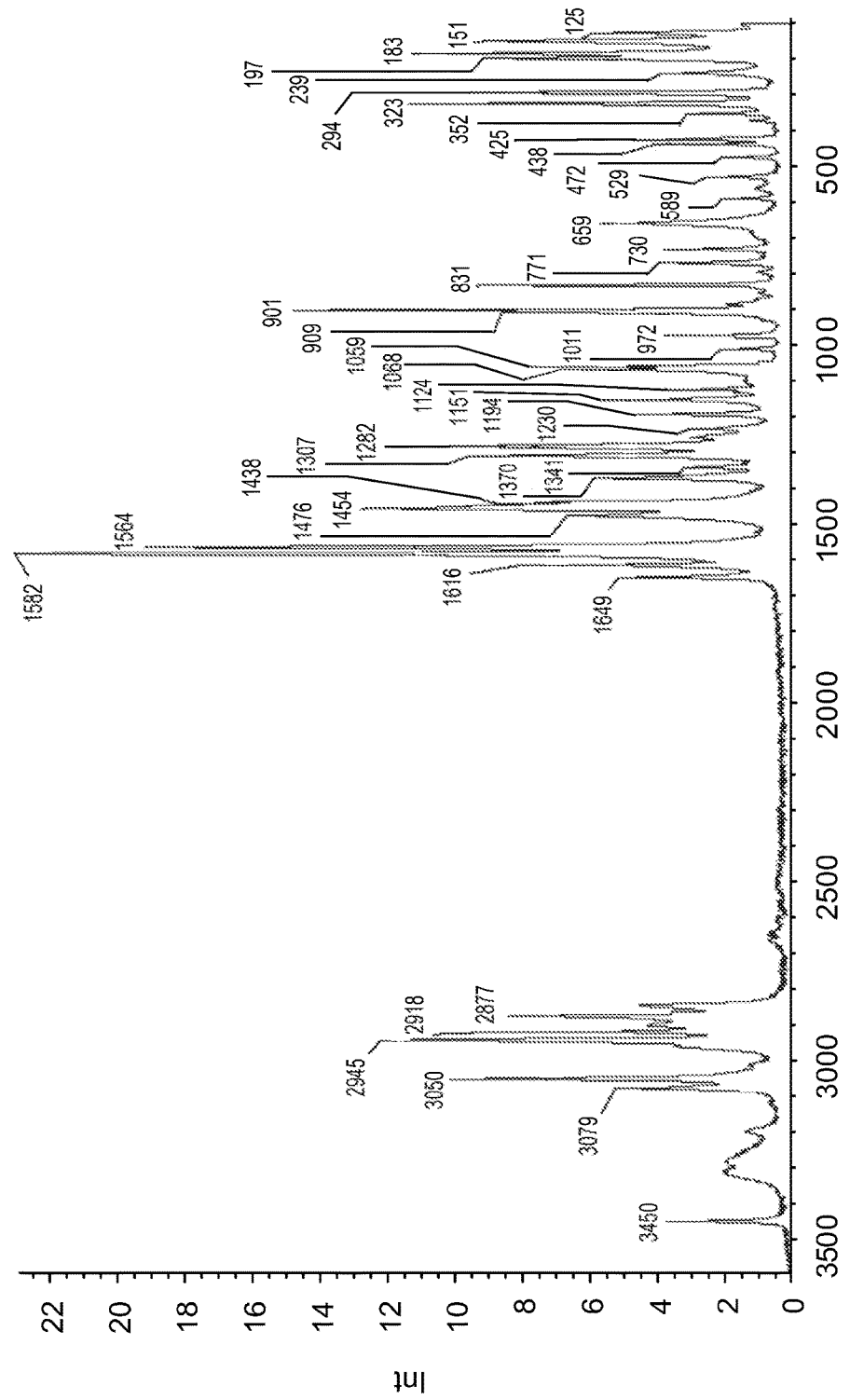
FIG. 5: Raman spectrum of form A
Figure 6:
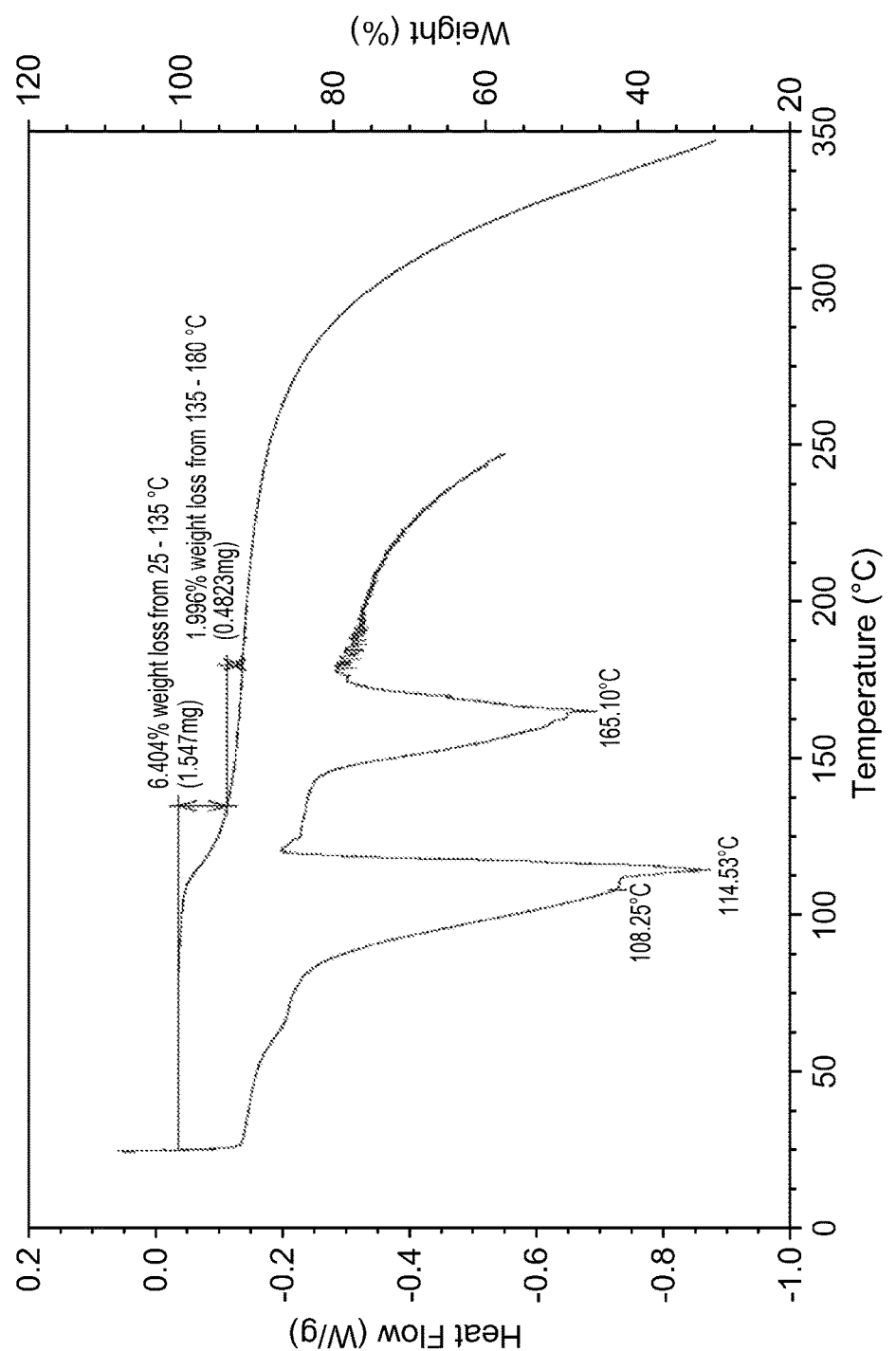
FIG. 6: DSC (upper) and TGA (lower) curves of form B isolated from acetone.
Figure 7:
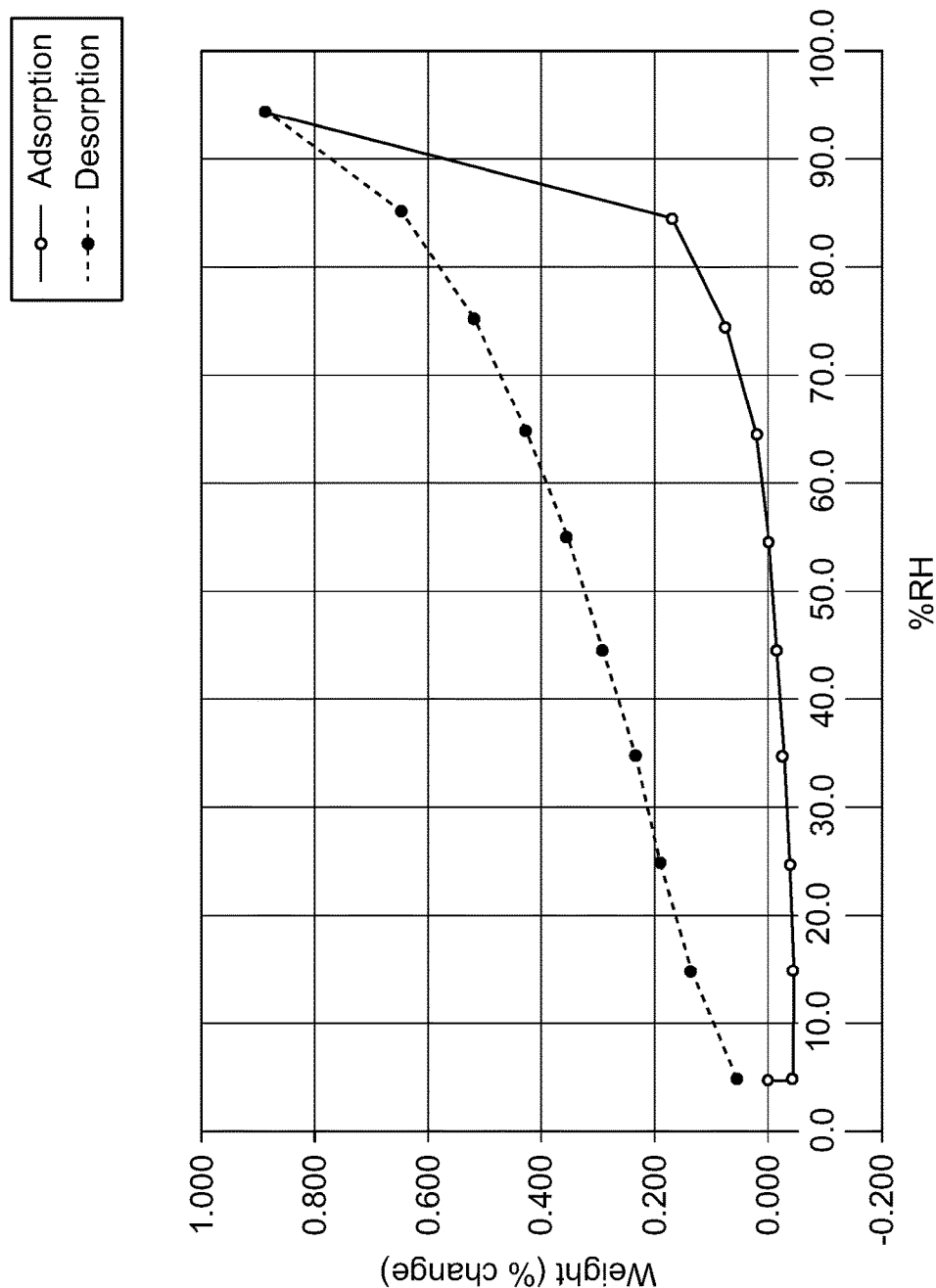
FIG. 7: Absorption-desorption spectrum of form B
Figure 8:
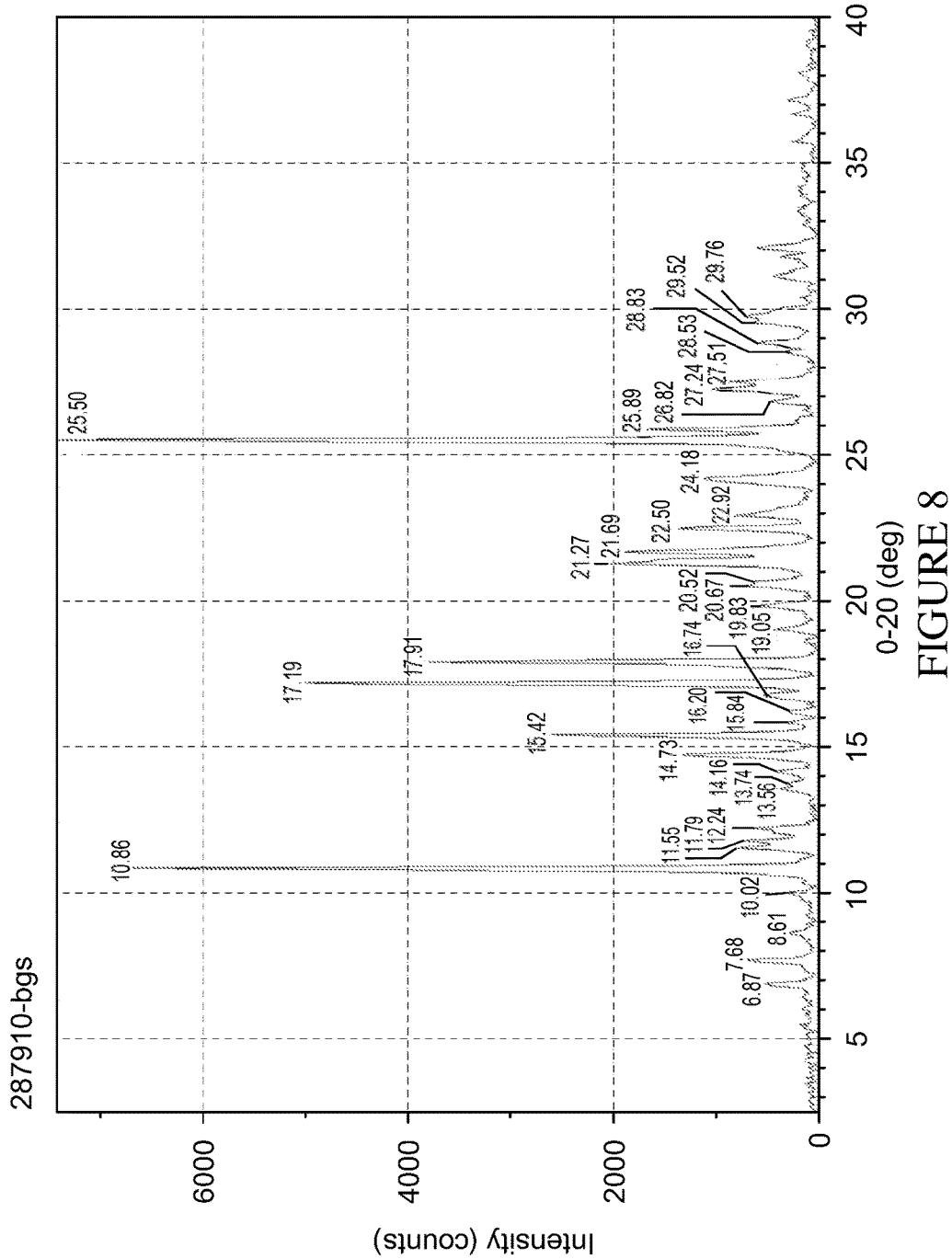
FIG. 8: XPRD spectrum of Form B. The peak assignments in this figure were picked automatically and no attempt was made to determine "representative" peaks.
Figure 9:
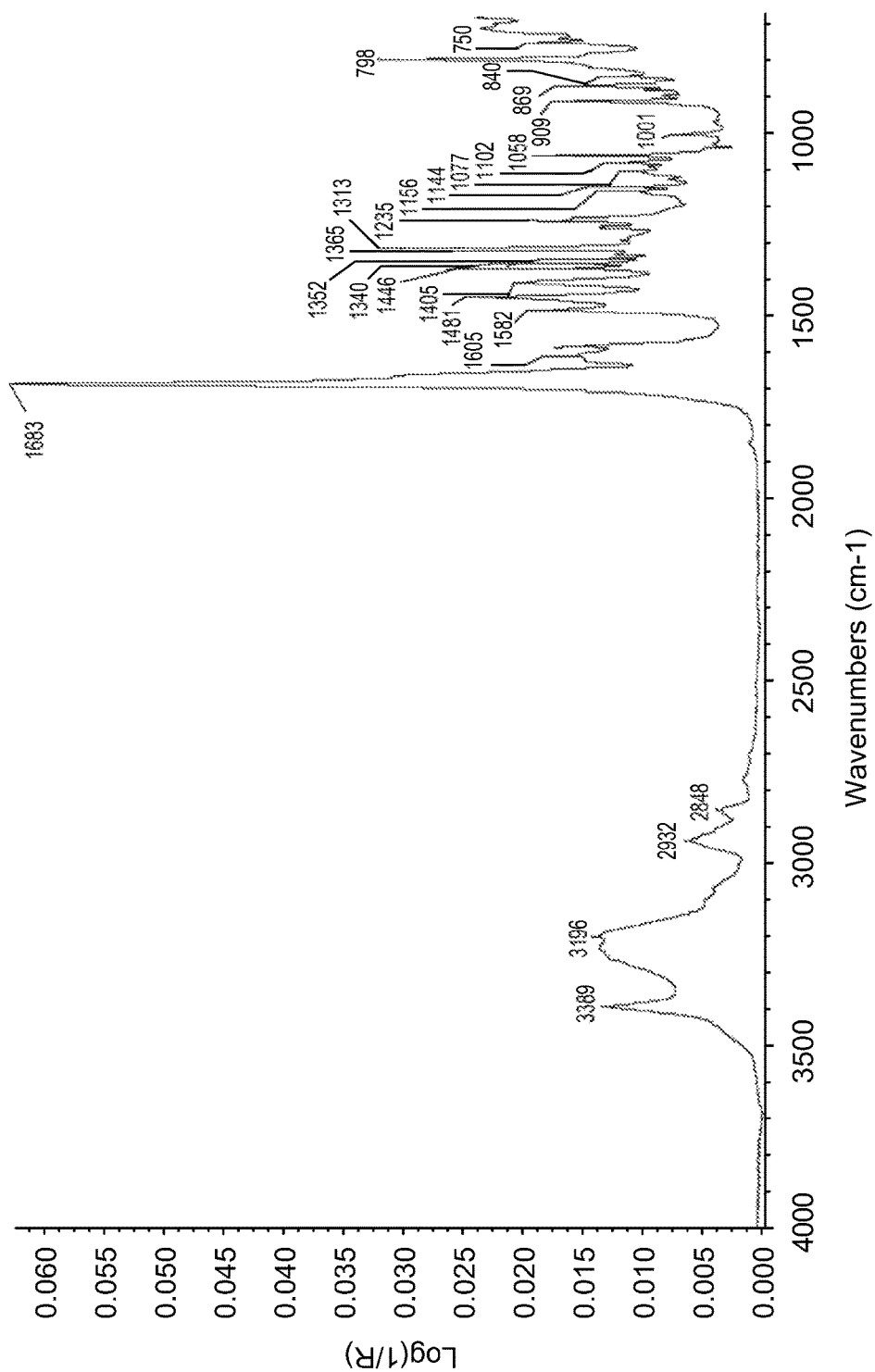
FIG. 9: IR spectrum of form B
Figure 10:
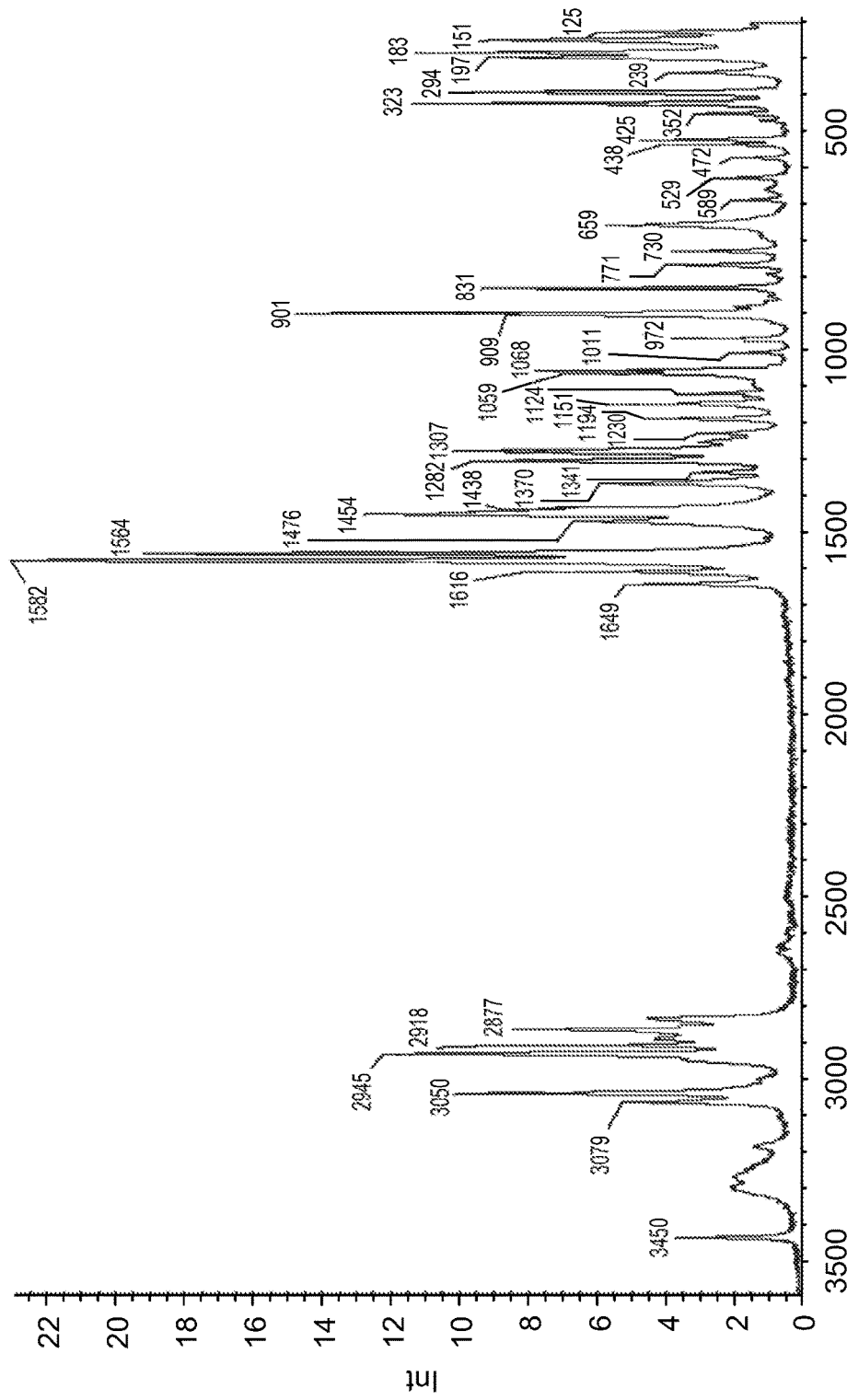
FIG. 10: Raman spectrum of form B
Figure 11:
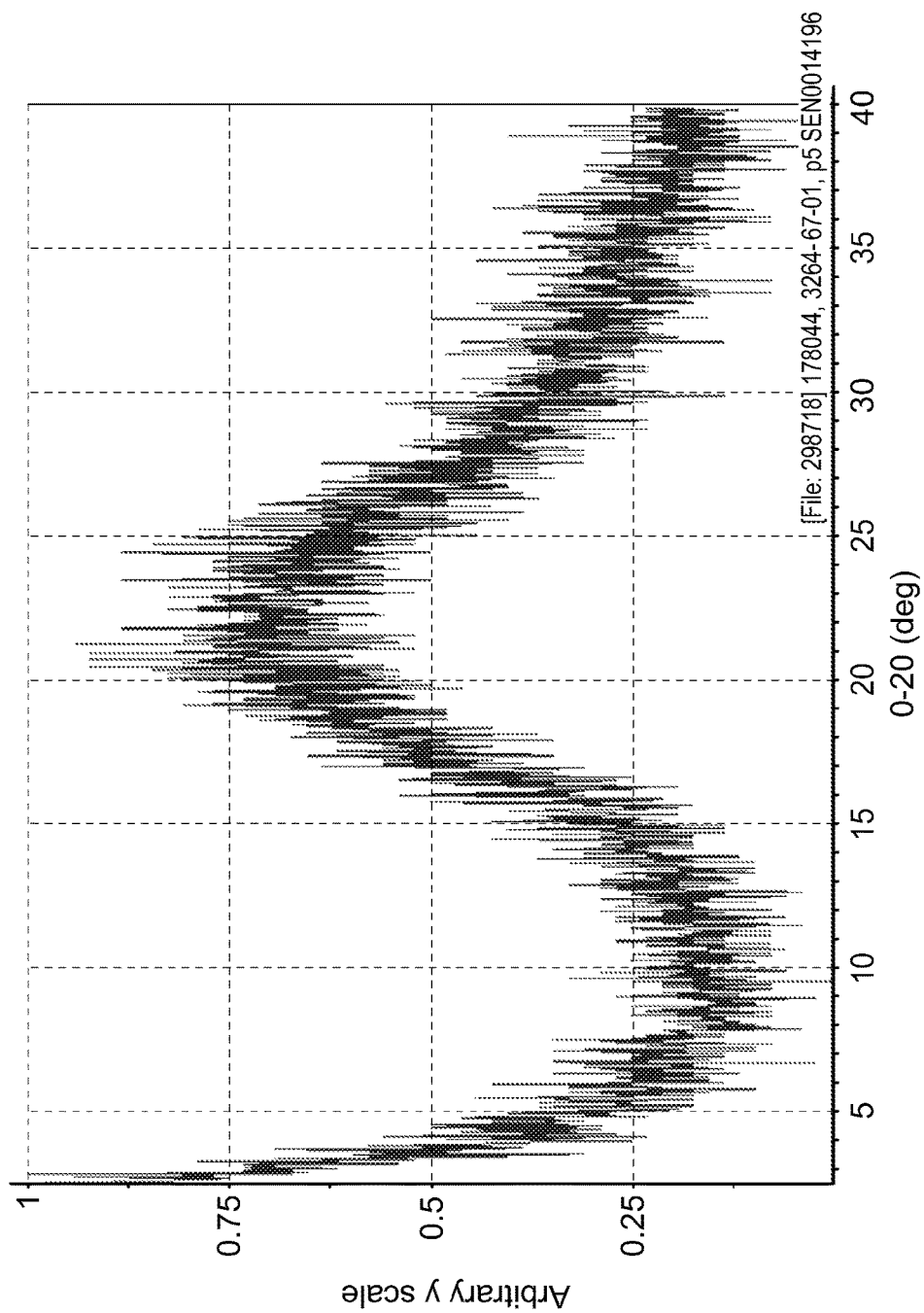
FIG. 11: XPRD spectrum of the amorphous form

Example 1: Stage 1 Procedure ((I'-c)-+(I'-a)) Involving DCM as Solvent

Ethyl-2-cyclohexanone-carboxylate (2 kg, 11.75 mol) and DCM (6 L) were charged to a 20 L jacketed reactor and cooled to 0-5° C. Bromine (1877.8 g, 11.75 mol, 1 equiv) was pumped in over 2.5 hours maintaining the reaction temperature at 0-5° C. The reaction solution was then held at 0-5° C. for a further 2 hours before sampling. (GC area %: 1.7% ethyl-2-cyclohexanone-carboxylate, 76.4% 3-bromo-2-oxo-cyclohexanecarboxylic acid ethyl ester).

The reaction was quenched with water (5 L) allowing the exotherm to take the temperature to 20-25° C. The organic layer (bottom, hazy yellow, 10.78 kg) was separated form the clear colourless aqueous layer (5.97 kg). The organic layer was washed with sat. sodium bicarbonate solution (4 kg) and then separated (organic (10.43 kg) and aqueous (4.2 kg)). The organic layer was stripped to an oil under reduced pressure and ethanol (2 L) charged. The ethanol was then removed by distillation at reduced pressure to give a orange oil (2950.9 g).

Yield of crude product=100.8%
Purity (GC area %)=2.4% keto ester, 6.6% unkn (9.6 min), 89.6% 3-bromo-2-oxo-cyclohexanecarboxylic acid ethyl ester.

Example 2: Stage 1 Procedure with No Solvent

Ethyl-2-cyclohexanone-carboxylate (497 kg) is cooled down to 0° C. and bromine is added over 9 h while stirring, keeping the temperature at 0°±10° C. After complete addition, the mixture is stirred at 0° C. for 4 h (content of starting material 2.8% by GC), then it is warmed up to 20° C. and nitrogen is bubbled through the reaction mixture to drive off the HBr gas. Then the reaction mixture is stirred for another 25 h at 5° C. (content of HBr 0.8% by titration). 6-chloro-2,3,4,9-tetrahydro-1H-carbazole-1-carboxylic acid ethyl ester is drummed off and stored at 0° C. prior to use as such in the subsequent step.

Yield of crude product: 730.4 kg (100%)
Purity (determined by 1H-NMR with 3,4-Dimethoxybenzene as internal standard). 87% w/w.

Example 3: Stage 2 Procedure ((I'-a)→(I'-b)) with No Intermediate Azeotropic Distillation 4-chloroaniline (2473.5 g, 19.39 mol, 2.1 equiv) and ethanol (13.8 L) were charged to a 20 L jacketed reactor and heated to reflux (80° C.). The 3-bromo-2-oxo-cyclohexanecarboxylic acid ethyl ester (2300 g, 9.23 mol, 1.0 equiv) was added over—3 hrs maintaining reflux (a sample was taken: 338.3 g, 2.2% of yield). The reaction was held at reflux and was deemed complete after 56 hours (HPLC area %: 2.9% intermediates, 88.7% 6-chloro-2,3,4,9-tetrahydro-1H-carbazole-1-carboxylic acid ethyl ester).

The solvent was removed by distillation keeping the temperature below 50° C. Cyclohexane (10.58 L) and water (4.6 L) was added to the residue and the mixture heated to 50-55° C. The dark purple aqueous layer was separated from the dark brown organic layer. The organic layer was washed with 2M HCl (3×4.6 L) at 50-55° C. and the organic layer sampled to determine aniline content (non-detected by LCMS, spec <1% wrt 6-chloro-2,3,4,9-tetrahydro-1H-carbazole-1-carboxylic acid ethyl ester). The organic layer was washed with sat. sodium chloride solution (1×4.6 L) followed by sat. sodium bicarbonate solution (1×4.6 L) and finally water (1×4.6 L) at 50-55° C. The dark brown solution was then dried by the azeotropic removal of water (KF=0.02% spec <0.5%). The solution was then cooled to 15° C. and then isolated by filtration. The filter cake was washed with cold cyclohexane (15° C.) and the damp green product was dried at 50° C. for 16 hours. The 6-chloro-2,3,4,9-tetrahydro-1H-carbazole-1-carboxylic acid ethyl ester solid was isolated as a green crystalline solid (1636 g).

Wt=1636 g, Yield=63.8% Purity LCMS (210 nm)=99.4%, HPLC (215 nm)=97.6%.

Example 4: Stage 2 Procedure with Two Intermediate Azeotropic Distillations

A solution of 4-chloroaniline (266 kg) in EtOH (1425 l) was warmed to reflux (76° C.) and 3-bromo-2-oxo-cyclohexanecarboxylic acid ethyl ester (240 kg) was added over 1 h 40 min, while stirring at reflux (76 to 80° C.). Reflux (80° C.) was maintained for 5 h, then EtOH (200 l) was added, and solvent (200 l) was distilled off. Then EtOH (140 l) was added followed by distilling off solvent (140 l). The reaction mixture was then heated at reflux for another 17 h, after which the solvent (1400 l) is distilled off at reduced pressure and 60±5° C.

Then cyclohexane (1122 l) is added while stirring at 45-59° C. To the cyclohexane solution, stirred at 52-59° C. is then added water (482 l). The phase are separated, and the aqueous phase is discarded. The organic phase (kept at 54-58° C.) is then washed five times with a mixture of water (184 l) and conc. HCl (48 l), followed by washing with water (240 l), sodium bicarbonate (25 kg) in water (250 l) solution and finally water (480 l).

Then more cyclohexane (453 l) is added to the warm (55-57° C.) solution, followed by evaporation of solvent (453 l) to azeotropically remove water. Then the reaction mixture is stepwise cooled to 40° C. over 2 h, to 10° C. over 2 h and kept at 5-10° C. for 1.5 h to crystallise 6-chloro-2,3,4,9-tetrahydro-1H-carbazole-1-carboxylic acid ethyl ester. After centrifugation, the solid is recrystallised once more from cyclohexane (731 l), centrifuged and drummed off without further drying for use in the subsequent step. Yield: 183 kg. LOD (determined by lab sample): 10%, Yield=70.8%, Purity (HPLC): 99.4%.

Example 5: Stage 3 Procedure ((I'-b)→+(I)) Using Ammonia in Methanolic Solution 6-chloro-2,3,4,9-tetrahydro-1H-carbazole-1-carboxylic acid ethyl ester and ammonia in methanol (7N) were charged to the 3 liter autoclave and heated to 60-65° C. (a pressure of 2.3 bar was reached). The reaction mixture was then held at this temperature for 48 hours then cooled to 20-25° C. and sampled for completion. The reaction was deemed complete (LCMS(210 nm, area %): 6-chloro-2,3,4,9-tetrahydro-1H-carbazole-1-carboxylic acid methyl ester 1.4%, 6-chloro-2,3,4,9-tetrahydro-1H-carbazole-1-carboxylic acid amide 96.7%: HPLC (215 nm, area %): 6-chloro-2,3,4,9-tetrahydro-1H-carbazole-1-carboxylic acid methyl ester 0.6%, 6-chloro-2,3,4,9-tetrahydro-1H-carbazole-1-carboxylic acid ethyl ester 0.3%, 6-chloro-2,3,4,9-tetrahydro-1H-carbazole-1-carboxylic acid amide 97.8%). The reaction solution was transferred to a 3 L flange reactor and nitrogen was bubbled through the solution via a sparge tube for 3 hours. During this process the product precipitated out of solution. The mixture was then heated to reflux and methanol (505 ml) was removed by distillation at atmospheric pressure (distillation started at 42° C. head T/46° C. pot T and was terminated at 60° C. head T/63° C. pot T). Water (270 ml) was then added slowly over 15 minutes maintaining the reaction temperature at reflux (the product precipitated during the addition). The mixture was cooled to 0-5° C. and held at this temperature for 1 hour. The product was isolated by filtration and the damp filter cake washed with cold (5° C.) methanol/water 1:1 (120 ml). The crude 6-chloro-2,3,4,9-tetrahydro-1H-carbazole-1-carboxylic acid amide was isolated as a damp grey crystalline solid (305.59 g).

Wt=305.59 g, Str=75.6% (taking LOD into account), Yield=231.02 g (86%).

The damp crude 6-chloro-2,3,4,9-tetrahydro-1H-carbazole-1-carboxylic acid amide (305.59 g, 231.02 g 100%) was heated to reflux (82° C., product dissolves at ~74° C.) in 2-propanol (1975.2 g). 2-Propanol (200 ml) was removed by distillation at atmospheric pressure and the solution cooled to ~60° C. The solution was then seeded and the product crystallised. The mixture was then held at 60° C. for 1 hour and then cooled slowly to 0-5° C. The mixture was held at this temperature for 1 hour. The product was isolated by filtration and the damp filter cake washed with cold (5° C.) IPA (250 ml). The damp solid was then dried for 16 hours at 60° C. to give an off-white crystalline solid (189.95 g).

Wt=189.95 g (82.2% for crystallisation, 70.7% for 6-chloro-2,3,4,9-tetrahydro-1H-carbazole-1-carboxylic acid amide overall).

Purity
LCMS (210 nm)=100%
HPLC (215 nm)=100%
Moisture content (by KF)=0.05%
LOD=0.5%

Example 6: Stage 3 Procedure Using Pure Ammonia

A solution of 6-chloro-2,3,4,9-tetrahydro-1H-carbazole-1-carboxylic acid ethyl ester (183 kg) in MeOH (850 l) in a pressure reactor was cooled to 5±5° C., and ammonia (328 kg) was added over 4 h while stirring at to 5±5° C. Then the temperature was increased to 45±5° C. (4 bar internal pressure) and kept at this temperature for 47 h (HPLC check: no s.m. left).

The solution was cooled to 0-10° C., filtered into a non-pressure reactor and warmed to 45±5° C. over 4 h and kept at this temperature for another 12 h to gas off the excess ammonia. After charcoal treatment (8 kg) at 60° C., filtration, washing with MeOH (150 l) and evaporation of solvent (300 l), water (200 l) is added and the mixture is cooled to 3±3° C. to precipitate 6-chloro-2,3,4,9-tetrahydro-1H-carbazole-1-carboxylic acid amide product. The solid is centrifuged and drummed off for the subsequent recrystallisation. Yield: 142 kg. With a LOD=16% this corresponds to 119 kg dry material (81.3% of theory).

This material, dissolved in methyethyl ketone (407 kg) is heated to reflux, and cyclohexane is added at to 68-77° C. over 15 min. The mixture is stirred at to 68° C. for 1.5 h, then it is cooled to 0° C. over 2 h. The solid is isolated by centrifugation (146 kg, wet).

The solid is suspended in 2-propanol heated to reflux within 2 h 20 min (complete dissolution), then cooled to 0±5° C. over 2.5 h and kept at to 0±5° C. for 1 h. The solid is centrifuged and then dried for 18 in a paddle dryer (to 20-49° C., 28-86 mbar) to give the final product (88.3 kg).

Example 7: Crystallization from Cyclohexane/MEK Followed by Re-Crystallisatrion from Isopropanol Affords Higher Purity Material than 2 Subsequent Crystallisations from Isopropanol Aliquots of the same batch ensuing from step b) (claim 8) were crystallised twice as set out the table below

| Method | Crude material ensuing from step e) | Material recovered after second crystillasation | Recovery yield | Purity (HPLC 230 nm) | Residual 4-chloroaniline (HPLC 221 nm) |
|---|---|---|---|---|---|
| Cyclohexane/MEK then isopropanol | 60 g | 41.7 g | 81.8% | 99.97% | <5 ppm |
| Twice from isopropanol | 20 g | 12.4 g | 82.2% | 99.91% | 26 ppm |

Tables 3 and 4: Form A stability data: Compound (I) in the form of Form A was packed in double bagged polythene bags (fastened with cable/security ties) and placed inside 3.6 L Curtec kegs (HDPE) to simulate typical drug substance storage conditions. Stability tests were performed at 40° C./75% RH (table 3) and 25° C./60% RH (table 4).

TABLE 3

| Stability tests | Specification | t = 0 | t = 1 month | t = 3 months | t = 6 months |
|---|---|---|---|---|---|
| Description | A white to off-white solid | Off-white solid | Off-white solid | Off-white solid | Off-white solid |
| Water content (by KF titration) | Not more than 0.5% w/w (Aquamicron AX, 2 minute delay) | <0.1% w/w | <0.1% w/w | 0.4% w/w | 0.1% w/w |
| DSC | Conforms to polymorph A (AS113/D/001) | Conforms | N/A | N/A | N/A |
| XRPD | Conforms to polymorph A (AS113/X/001) | Conforms | N/A | N/A | Conforms |
| Impurity content (by HPLC) | Total impurities not more than 2.0% area | 0.31% area | 0.25% area | 0.25% area | 0.33% area |
|  | No single impurity greater than 0.50% area | Conforms | Conforms | Conforms | Conforms |
| Assay (by HPLC) | 98.0-102.0% w/w on an anhydrous and solvent free-basis | 99.7% w/w | 98.9% w/w | 99.4% w/w | 99.0% w/w |

TABLE 4

| Stability tests | Specification | t = 0 | t = 1 month | t = 3 months | t = 6 months | t = 9 months | t = 12 months | t = 18 months | t = 24 months |
|---|---|---|---|---|---|---|---|---|---|
| Description | A white to off-white solid | Off-white solid | Off-white solid | Off-white solid | Off-white solid | Off-white solid | Off-white solid | Off-white solid | Off-white solid |
| Water content (by KF titration) | Not more than 0.5% w/w (Aquamicron AX, 2 minute delay) | <0.1% w/w | <0.1% w/w | 0.2% w/w | 0.1% w/w | <0.1% w/w | 0.1% w/w | 0.1% w/w | <0.1% w/w |
| DSC | Conforms to polymorph A | Conforms | N/A | N/A | Conforms | N/A | Conforms | N/A | Conforms |
| XRPD | Conforms to polymorph | Conforms | N/A | N/A | Conforms | N/A | Conforms | N/A | Conforms |
| Impurity content(by HPLC) | Total impurities not more than 2.0% area | 0.31% area | 0.54% area | 0.22% area | 0.32% area | 0.29% area | 0.27% area | 026% area ** | 0.39% area |
|  | No single impurity greater than 0.50% area | Conforms | Conforms | Conforms | Conforms | Conforms | Conforms | Conforms | Conforms |
| Assay (by HPLC) | 98.0-102.0% w/w on an anhydrous and solvent | 99.7% w/w oastb | 99.0% w/w | 99.1% w/w | 98.7% w/w | 99.4% w/w | 99.0% w/w | 98.6% w/w | 98.2% w/w |

The invention claimed is:

1. A process for the preparation of compound (I'-b) on a kg-scale and larger, wherein compound (I'-b) is prepared according to the following scheme:

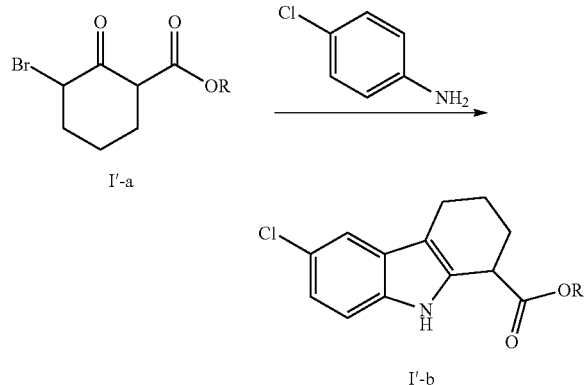

wherein R is a $C_1$-$C_6$ linear alkyl chain, $C_1$-$C_6$ branched alkyl chain, or cycloalkyl, said process being characterised in that the reaction between (I'-a) and 4-chloroaniline is performed under heating in a solvent which forms an azeotropic mixture with water, and wherein the ensuing water is removed by azeotropic distillation.

2. A process according to claim 1, wherein said solvent is selected from the group consisting of xylenes, chlorobenzene, cyclohexane, ethyl acetate, MTBE, toluene and ethanol.

3. A process according to claim 1, further comprising crystallization of compound (I'-b) from an apolar solvent.

4. A process according to claim 3, wherein said apolar solvent is cyclohexane.

5. The process according to claim 1 further comprising reacting compound (I'-b) with ammonia to provide compound (I)

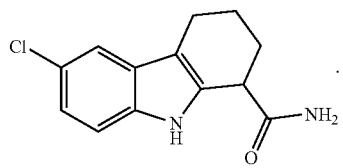

6. A process according to claim 5, wherein said reaction is carried out in a solvent selected from the group consisting of ethanol and methanol.

7. A process according to claim 5, wherein compound (I) is further processed by:
 a) removing any unreacted ammonia from the reaction mixture;
 b) precipitating compound (I) from the reaction mixture;
 c) recrystallising the precipitate from a suitable solvent so as to obtain compound (I) in crystalline form A.

8. A process according to claim 7, wherein step a) is performed by evaporation under reduced pressure and/or heating and/or sparging the reaction mixture with an inert gas.

9. A process according to claim 7, wherein step b) is performed by addition of water to the reaction mixture.

10. A process according to claim 7, wherein the solvent used in step c) is selected from the group consisting of ethyl acetate, water, methanol, ethanol and isopropanol.

11. A process according to claim 7, further comprising crystallizing the crude precipitate ensuing from step b) from a MEK/cyclohexane solvent mixture before performing step c).

12. A process according to claim 1, wherein compound (I'-a) is obtained by reacting equimolar amounts of bromine and a compound of formula (I'-c), at 0-5° C. in DCM:

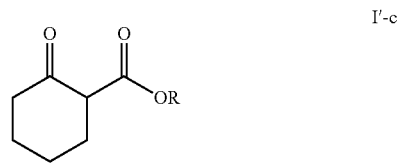

wherein R is as defined in claim 1.

13. A process according to claim 1, wherein compound (I-a') is obtained by slow addition, under stirring, of gaseous bromine to a solvent-free equimolar amount of compound (I'-c), at 0-10° C.:

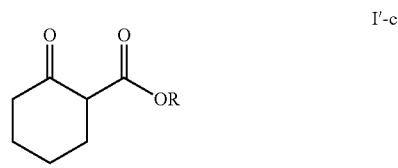

wherein R is as defined in claim 1.

14. A process according to claim 1, wherein R is ethyl.

15. A process according to claim 1, wherein said solvent is ethanol.

16. A process according to claim 7, wherein the solvent used in step c) is isopropanol.

17. A process according to claim 1, wherein the ensuing water is removed by an intermediate azeotropic distillation before completion of the reaction.

18. A process according to claim 17, wherein the ensuing water is removed by at least two intermediate azeotropic distillation steps.

* * * * *